United States Patent
Takahashi et al.

(10) Patent No.: US 6,896,980 B2
(45) Date of Patent: May 24, 2005

(54) WATER-SCAVENGING AGENT FOR AN ORGANIC ELECTROLUMINESCENT DEVICE AND ORGANIC ELECTROLUMINESCENT DEVICE COMPRISING SAME

(75) Inventors: Hisamitsu Takahashi, Chiba (JP); Shigeru Hieda, Chiba (JP); Yoshihisa Tsuruoka, Chiba (JP); Satoshi Tanaka, Chiba (JP)

(73) Assignee: Futaba Corporation, Chiba (JP)

( * ) Notice: Subject to any disclaimer, the term of this patent is extended or adjusted under 35 U.S.C. 154(b) by 0 days.

(21) Appl. No.: 10/659,255

(22) Filed: Sep. 11, 2003

(65) Prior Publication Data

US 2004/0056232 A1 Mar. 25, 2004

(30) Foreign Application Priority Data

Sep. 12, 2002 (JP) ........................................ 2002-267138

(51) Int. Cl.[7] .......................... C02F 05/10; H05B 33/00
(52) U.S. Cl. .......................... 428/690; 428/917; 428/76; 313/504; 313/512; 257/100; 106/252; 556/1; 546/2; 252/180
(58) Field of Search .................................. 428/690, 917, 428/76; 313/504, 512; 257/100; 106/252; 556/1; 546/2; 252/180

(56) References Cited

PUBLICATIONS

Monograph Series of the International Conferences on Coordination Chemistry held periodically at Smolenice in Slovakia, 3(Progress in Coordination and Organometallic Chemistry), p. 233–238 (1997).*
Journal of Indian Chemistry, 61(8), p. 697–698, (1984).*
Inorganica Chimica Acta, 173(1), pp. 121–125, (1990).*
Koordination Khimiya, 9(3), p. 319–321, (1983).*

ACS/STN database (2004) 1 page description of "Monograph Series of the International Conferences on Coordination Chemistry held periodically at Smolenice in Slovakia, 3(Progress in Coordination and Organometallic Chemistry), p. 233–238, (1997)".*
ACS/STN database (2004) 1 page description of "Journal of the Indian Chemical Society, 61(8), p. 697–698, (1984)".*
ACS/STN database (2004) 1 page description of "Inorganica Chimica Acta, 173(1), p. 121–125, (1990)".*
ACS/STN database (2004) 1 page description of "Koordinatsionnaya Khimiya, 9(3), p. 319–321, (1983)".*

* cited by examiner

Primary Examiner—Dawn Garrett
(74) Attorney, Agent, or Firm—Bacon & Thomas PLLC

(57) ABSTRACT

A novel water-scavenging agent of the present invention comprising a compound of formula (I) as a primary component can be dissolved in a polar solvent and coated by a screen printing method, and the inventive organic EL device comprising same can maintain stable luminescent characteristics for a prolonged time:

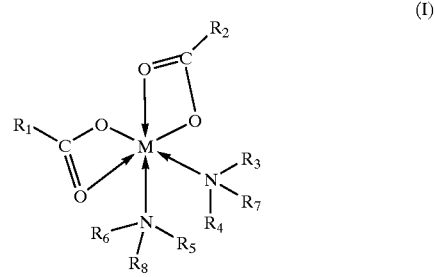

(I)

wherein,
$R_1$, $R_2$, $R_3$, $R_4$, $R_5$ and $R_6$ are each independently hydrogen; halogen; alkyl, aryl, cycloalkyl or hetero-ring, optionally substituted with at least one halogen atom, and
M is a metal having a coordination number of 6.

4 Claims, 4 Drawing Sheets

WATER-SCAVENGING AGENT FOR AN ORGANIC ELECTROLUMINESCENT DEVICE AND ORGANIC ELECTROLUMINESCENT DEVICE COMPRISING SAME

FIELD OF THE INVENTION

The present invention relates to an organic EL device, and more particularly to an improved water-scavenging agent which is held inside an organic EL device for maintaining stable luminescent characteristics for a prolonged time by preventing the adverse effect of moisture or oxygen.

BACKGROUND OF THE INVENTION

Generally, an organic EL device has the structure of a laminated luminescent part comprising an anode, a cathode, and an organic luminescent thin layer containing a fluorescent organic compound arranged between the two electrodes. In such an organic EL device, holes and electrons are injected into the fluorescent organic compound-containing thin layer, which recombine to generate exitons, and light (fluorescence, phosphorescence) is emitted when the generated exitons lose their excitation energy.

The biggest issue involved in the organic EL device is the enhancement of its operating life. One of various reasons causing decreased luminescent life is the appearance of non-luminescent dots referred to as "dark spots", which tend to grow with the operating time to lower the brightness of the luminescent part. When such non-luminescent dots grow to the size of several 10 μm or larger, they can be recognized with the naked eye, which marks the end of the product life. It is known that such dark spots are generated and grow by the action of residual moisture or oxygen remaining inside the EL enclosed in a sealing case.

Consequently, it is necessary to remove moisture from inside of the sealing case of an organic EL device, and also to purify organic materials used in the luminescent part to remove moisture therefrom. In order to prevent moisture from remaining inside the sealing case, the processes of forming the luminescent part on a substrate plate in a vacuum chamber and sealing the substrate plate having the luminescent part with an enclosing cap are performed in an utmost dry state. However, it is not possible to completely eliminate moisture from said manufacturing processes, and therefore, the generation and growth of dark spots cannot be completely suppressed.

Thus, one of the most important problem to be solved in the field of organic EL device is how to prolong the use life by way of preventing the generation of dark spots or suppressing further growth of small dark spots. In this connection, an organic EL device comprising an inorganic drying agent disposed inside the sealing case is commercially available and disclosed, for example, in Japanese Publication No. 1997-148066 ('Patent reference 1').

Also, to solve the problem associated with the powder form of an inorganic drying means disclosed in Patent reference 1, Japanese Publication No. 2002-33187 ('Patent reference 2') teaches a technique of forming a layer of an organo-metallic compound having high reactivity toward moisture.

The organic EL device disclosed in Patent reference 2, as shown in FIG. 3, comprises an organic luminescent part having an organic luminescent layer (34) sandwiched between an anode (35) and a cathode (36) disposed on a glass substrate plate (32), wherein the organic luminescent layer (34) has a laminated structure of three layers comprising a hole injection layer (34a), a hole transport layer (34b) and a luminescent layer/electron transport layer (34c). The organic luminescent layer (34) is encased in a sealing case which consists of the glass substrate plate (32), an enclosing cap (33) and a sealing part (38), together with a water-scavenging agent layer (37) which protects the luminescent layer (34) from water. The water-scavenging agent layer (37) is a thin layer of an organo-metallic compound such as the compounds of formulae (III), (IV) and (V):

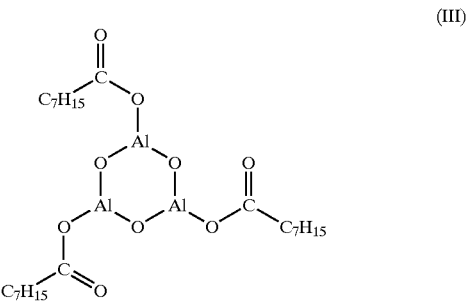

(III)

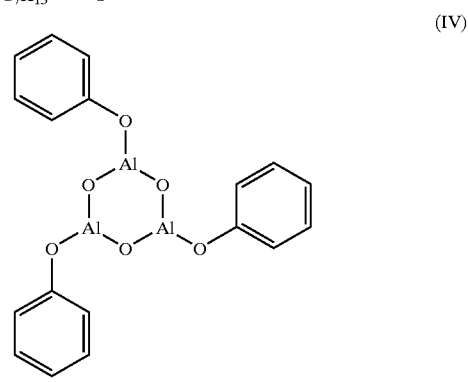

(IV)

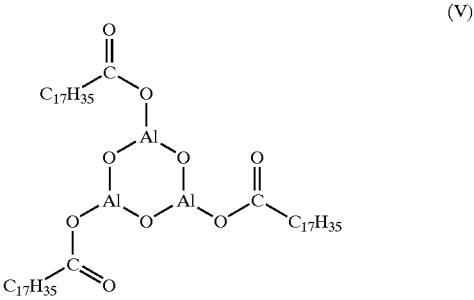

(V)

The water-scavenging agent layer (37) may be obtained by dissolving the compound of formula (III), (IV) or (V) in an organic solvent and coating the solution on the inner surface of the enclosing cap (33) made of a flat glass plate to form a 10 μm thick film.

If necessary, the flat enclosing cap (33) is processed so as to form a 0.2 to 0.25 mm deep intaglio, or, as shown in FIG. 4, the enclosing cap (43) is manufactured in the form of an intagliated part (49), and a water-scavenging agent layer (47) is encased in the formed intaglio.

Conventional organo-metallic compounds which can be used to form the water-scavenging agent layer (37), e.g., the compounds of formulae (III), (IV) and (V), are dissolved in an organic solvent and the resulting solution is coated to form a film. Such compounds readily dissolve in a hydrocarbon-based solvent, but not in a polar solvent. Therefore, it is difficult to coat the conventional organo-metallic compounds by a screen printing method which requires the use of an acryl-based polymer dissolved in a polar solvent such as butylcarbitol and terpineol.

SUMMARY OF THE INVENTION

Accordingly, it is a primary object of the present invention to provide a novel water-scavenging agent which readily dissolves in a polar solvent, and therefore, is coatable by a screen printing method.

It is a further object of the present invention to provide a thin organic EL device employing said water-scavenging agent.

In accordance with one aspect of the present invention, there is provided a water-scavenging agent for an organic EL device comprising a compound of formula (I) as a primary component:

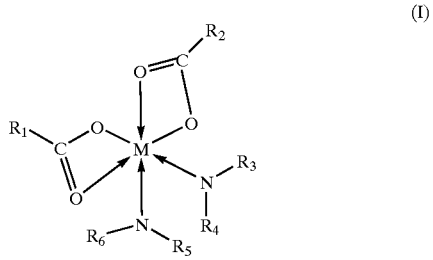

(I)

wherein, $R_1$, $R_2$, $R_3$, $R_4$, $R_5$ and $R_6$ are each independently hydrogen; halogen; alkyl, aryl, cycloalkyl or hetero-ring, optionally substituted with at least one halogen atom, and M is a metal having a coordination number of 6.

In accordance with another aspect of the present invention, there is provided an organic EL device which comprises a glass substrate plate having an organic luminescent part, a sealing case having a cap to be sealed with said glass plate to enclose said organic luminescent part and a water-scavenging means installed inside said sealing case, the water-scavenging means containing the water-scavenging agent.

BRIEF DESCRIPTION OF THE DRAWINGS

The above and other objects and features of the present invention will become apparent from the following description, when taken in conjunction with the accompanying drawings, which respectively show.

Figure 1:
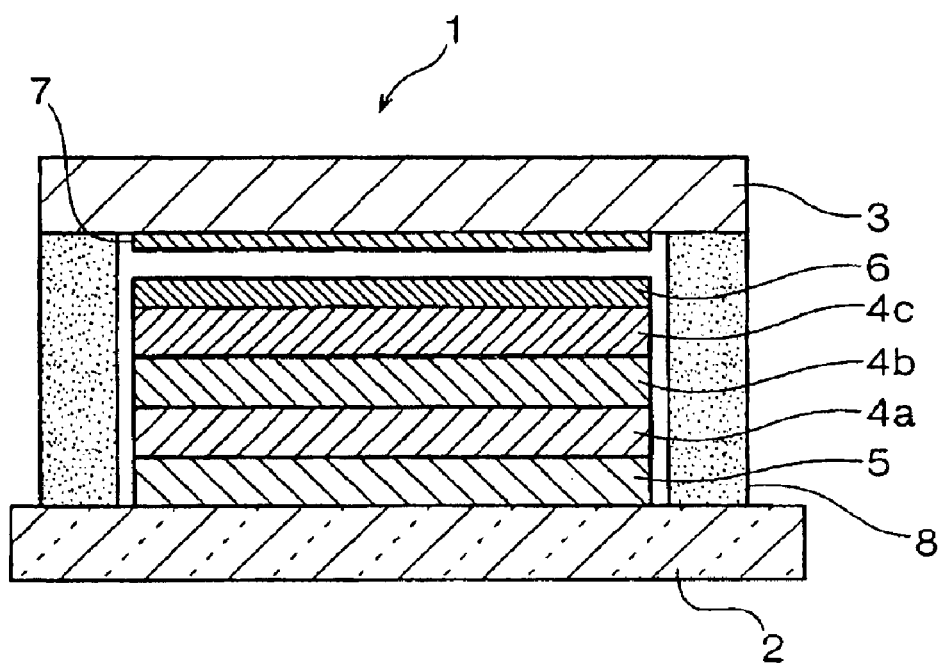
FIG. 1: a schematic diagram of the organic EL device in accordance with one embodiment of the present invention.

BRIEF DESCRIPTION ON DRAWING MARKS 1, 31, 41: organic EL device
2, 32, 42: glass substrate plate
3, 33, 43: enclosing cap
4, 34, 44: organic luminescent layer
5, 35, 45: anode
6, 36, 46: cathode
7, 37, 47: water-scavenging means
8, 38, 48: adhesive
49: intagliated part
50: a sheet of coverlet

DETAILED DESCRIPTION OF THE INVENTION

Figure 2:
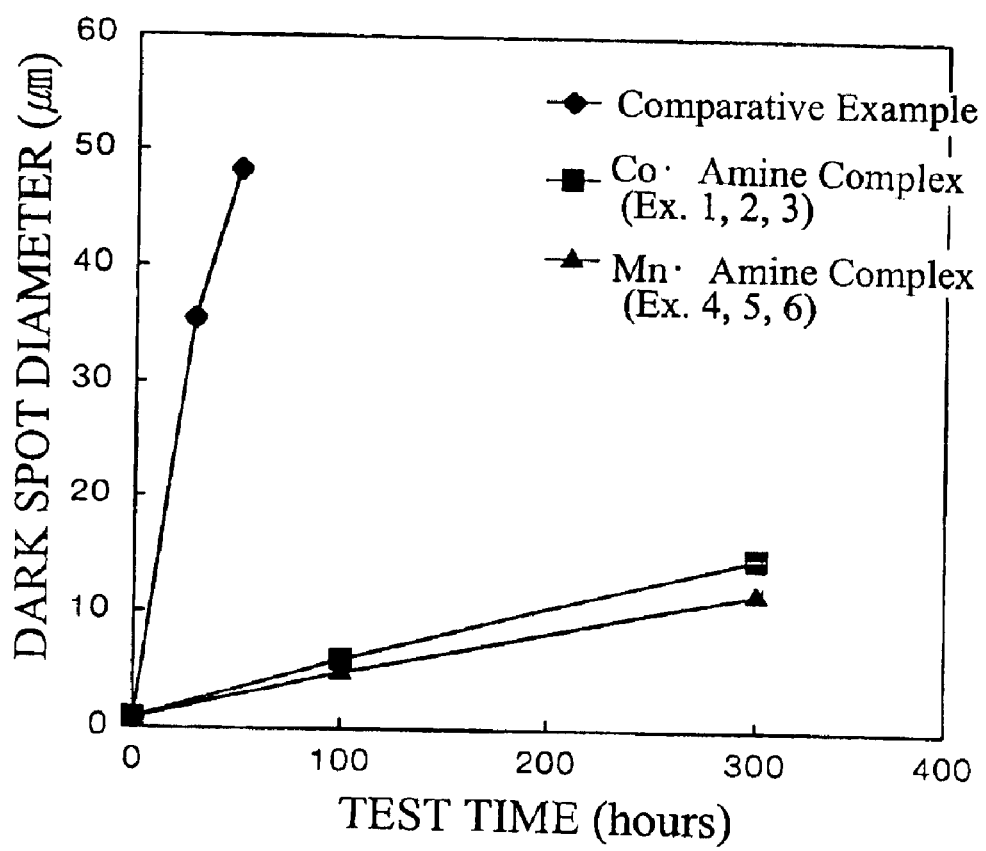
FIG. 2: graphs exhibiting the growth of dark spots with time, observed in Examples and Comparative Example.
Figure 3:
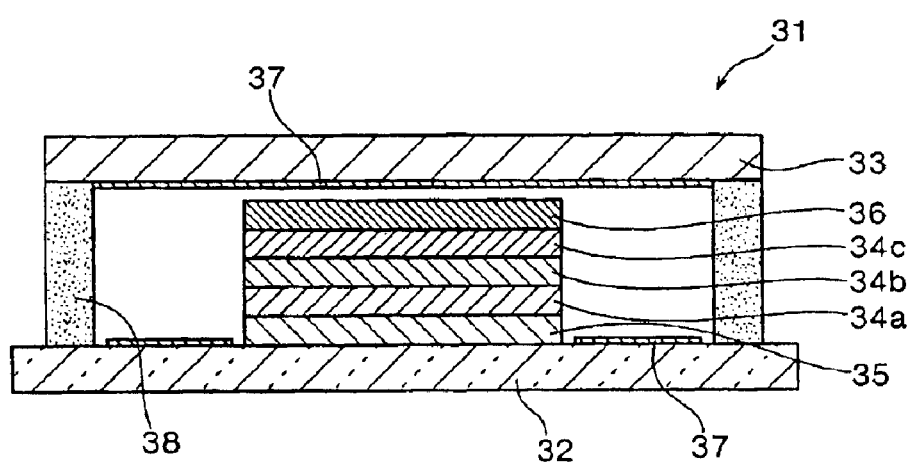
FIGS. 3 and 4: schematic diagrams of conventional organic EL devices.
Figure 4:
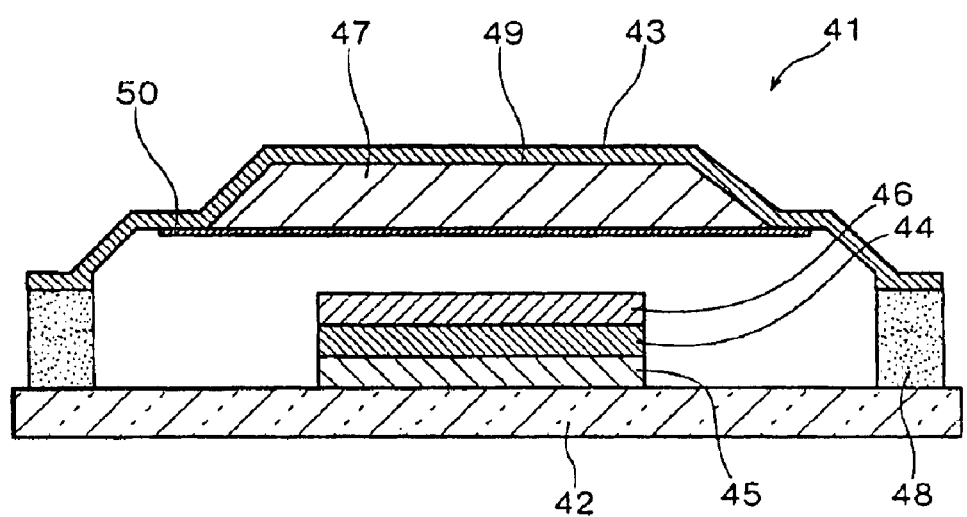

FIG. 1 depicts a schematic diagram of an organic EL device in accordance with one embodiment of the present invention, and FIG. 2, plots exhibiting the increase in the dark spot diameter with the operating lighting time for the organic EL devices having the water-scavengers, prepared in Examples 1 to 6, and the organic EL device having no water-scavenger, prepared in Comparative Example.

As shown in FIG. 1, this organic EL device (1) comprises a rectangular glass substrate plate (2) having suitable insulation and light-transmission properties. An anode (5) made of a transparent conducting material is patterned on the inner surface of the glass plate (2). The transparent conducting material, e.g., an ITO layer, is formed on the whole surface of the glass plate (2), e.g., by physical vapor deposition (PVD) such as vacuum vapor deposition and sputtering, and then patterned to a desired shape by photolithography to prepare an anode (5). A part of the anode (5) is extended to the end of the glass plate (2) to be connected to an operating circuit which is not shown in the figure.

An organic luminescent layer (4), a thin layer of an organic compound, is laminated on the anode (5), e.g., by PVD such as molecular ray deposition and resistance heating, Referring to FIG. 1, the organic luminescent layer (4) has three laminated layers consisting of a hole injection layer (4a) of CuPu formed in a thickness of several 10 nm on the anode (5), a hole transport layer (4b) of bis((N-(1-naphtyl-n-phenyl))benzidine (α-NPD) formed in a thickness of several 10 nm on the hole injection layer (4a), and a luminescent layer/electron transport layer (4c) of tris(8-quinolinolato)aluminum ($Alq_3$) formed in a thickness of several 10 nm on the hole transport layer (4b). Thus, the organic luminescent part is a five-layer laminate of the anode (5), the organic luminescent part (4) and a cathode (6).

The cathode (6) shown in FIG. 1 is a thin layer of a metal formed on the organic luminescent $Alq_3$ layer (4). Exemplary metals that can be used to form the cathode are those metals having a low working coefficient, e.g., Al, Li, Mg and In, and alloys, e.g., Al—Li and Mg—Ag. The cathode (6) may be formed in a thick layer ranging from 10 to several 100 nm, preferably from 50 to 200 nm. A part of the cathode (6) is extended to the end of the glass plate (2) to be connected to an operating circuit which is not shown in the figure.

A sealing part made of a UV-curable adhesive is formed at the outer periphery of an enclosing cap (3), a rectangular glass plate, and a water-scavenging agent layer (7) is disposed in the inner side of the enclosing cap (3).

The organo-metallic compound of formula (I) is used as a water-scavenging agent for the water-scavenging agent layer (7). The organo-metallic compound of formula (i), $M(COOR_1)(COOR_2)(NR_3R_4)(NR_5R_6)$, has a structure in which the oxygen atoms of the carboxylic groups and the nitrogen atoms of the amino groups of amines are coordinated to metal M having a coordination number of 6.

The metal complex having the structure of formula (I) of the present invention was designed based on the following.

The conventional organo-metallic complex of formula (III) reacts with moisture as shown in Reaction Scheme A:

Reaction Scheme A

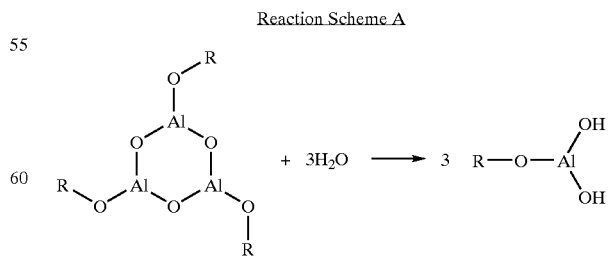

wherein, R is $(CO)C_7H_{15}$.

In Reaction Scheme A, the cyclic part of the metal complex opens as it reacts with water molecules. In this reaction which may be called an addition or substitution reaction, the metal complex chemically absorbs the water molecules. In accordance with a proposed reaction mechanism, the Al—O bond of the metal complex is polarized as $Al^{d+}$—$O^{d-}$. The water molecules attack and break the aluminum-oxygen bond. For enhancing the reaction between aluminum and water, it is preferable that such polarization be larger and the steric hindrance of the ligand, smaller.

The polarization of the aluminum-oxygen bond may become larger when at least two different ligands coordinate to one metal. For example, the nitrogen atom of an amine-based ligand donates electrons to the metal, nitrogen becoming positively polarized. In addition, a carboxylic acid ligand is expected to pull electrons to negatively polarize the metal. The resultant metal complex gains a dipole moment generated by such large polarization.

Based on the above-mentioned theory, the present inventors have designed the organic compound of formula (I) which can easily react with water molecules. In this organic compound, amino and carboxylic groups coordinate with the metal through ionic and chelate bonds.

It has been experimentally found that the water-scavenging ability of the organo-metallic compound of formula (I) depends on the kind of amine ligand used. Representative examples of the amine ligand include 2,2'-bipyridyl(BPY), 1,10-phenantronine(PHEN) and pyridine (PY) groups. Other amines that can also be used in the prevent invention are aliphatic aminoalcohols such as monoethanolamine(MEA), diethanolamine(DEA), methyldiethanolamine(MDEA) and butyldiethanolamine (BDEA), and aliphatic amines such as diethylamine(DETA), triethylamine(TETA) and n-butylamine(NBTA).

The inventive water-scavenging agent can be dissolved in an organic solvent and the resulting solution may be used for coating. Suitable organic solvents are hydrocarbons including xylene, toluene, heptane, hexane, cyclohexane and mineralspirit; alcohols including methanol, ethanol, propanol and cyclohexanol; ketones including methylketone, methylisobutylketone and cyclohexanone; and ethers including propylether, methylcellosolve, cellosolve, butylcellosolve, methylcarbitol and butylcarbitol.

As described above, the solvent that may be used for coating of the organo-metallic compound of formula (I) is not limited to a hydrocarbon-based solvent. The compound of formula (I) readily dissolves in a polar organic solvent such as butylcarbitol and terpineol, and the solution can be used for coating by a screen printing method, wherein a binder such as cellulose-based polymers such as ethylcellulose and hydroxypropylcellulose, and acryl-based polymers such as polymethacrylate and polyacrylate may be used.

Besides the screen printing method, the coating layer of the compound of formula (I) may be formed by various methods including spinning, spraying, dispensing, ink jet coating, doctor blading, off-set printing and the like.

In addition, a suitable dry means that may be used for drying the coating layer includes an oven, vacuum oven, autoclave, original infrared ray belt and furnace. Generally, these drying means are operated under a dry nitrogen atmosphere.

The sealing process in accordance with the present invention is performed by coating, e.g., a UV-curable resin adhesive as a sealant (8) at the outer periphery of the rectangular enclosing cap (3) under a dry atmosphere such as an inert gas from which the moisture is thoroughly removed, and then seal-tightly attaching the enclosing cap (3) to the glass substrate plate (2) so that the anode (5), the organic luminescent layer (4) and the cathode (6) are protected by the enclosing cap (3).

The water-scavenging function of the inventive organo-metallic compound of formula (I) is described as follows.

The inventive organo-metallic compound of formula (I) captures water molecules through a substitution reaction. Specifically, 2 moles of water molecule remaining in the organic luminescent case react with 1 mole of the organo-metallic compound to form a hydroxide. The present inventors have found that the organo-metallic compound of formula (I) exhibits an improved water-scavenging capability as compared with the conventional compounds used for an organic EL device.

In formula (I), $R_1$, $R_2$, $R_3$, $R_4$, $R_5$ and $R_6$ are each independently hydrogen, halogen, alkyl, aryl, cycloalkyl or hetero-ring, optionally substituted with at least one halogen atom. They may also be interlinked to form various forms of polymers.

The central metal M is a metal having a coordination number of 6 and a representative example thereof is cobalt.

Co(COOR')2(BPY), one of the inventive organo-metallic compounds, has the structure of formula (II), wherein M is cobalt and the amine ligand is 2,2'-bipyridyl(BPY):

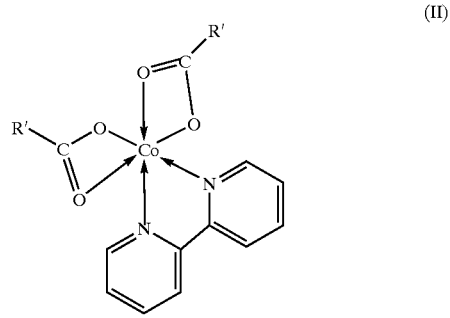

(II)

wherein, R' has the same meaning as $R_1$ to $R_6$.

Representative examples of the acyl group shown in formula (II) include formyl, acetyl, propiol, isobutyryl, valeryl, isovaleryl, pivaloyl, lauroyl, myristoyl, palmitoyl, stearoyl, oxaryl, maronyl, succinyl, tartaryl, poyl, pimeroyl, suberoyl, azelaoyl, cebacoyl, acryloyl, propioroyl, methacryloyl, crotonoyl, isocrotonoyl, oleoyl, elaidoyl, maleoyl, fumaroyl, citraconoyl, mesaconoyl, camphoroyl, benzoyl, phthaloyl, isophthaloyl, terephthaloyl, naphtoyl, toluoyl, hydroatropoyl, atropoyl, cinnamoyl, proyl, thenoyl, nicotinoyl, isonicotinoyl, glycoroyl, lactoyl, glyceroyl, tartronoyl, maloyl, tartaroyl, tropoyl, zendiroyl, sartiroyl, anisoyl, vaniroyl, veratroyl, piperoniroyl, protokacteoyl, galloyl, glyoxyroyl, pyruvoyl, acetoacetyl, mesoxaryl, mesoxaro, oxalacetyl, oxalaceto and levulinoyl groups, and they may be optionally substituted with fluorine, chlorine, brome or iodine.

The inventive compound of formula (II) used as a water-scavenging agent reacts with water as shown in Reaction Scheme B:

Reaction Scheme B

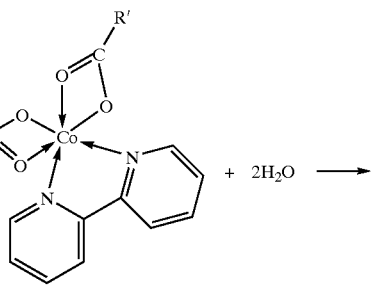

+ 2H$_2$O ⟶

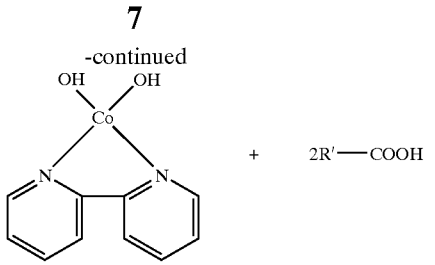

wherein, R' has the same meaning as defined above.

The inventive organo-metallic compound of formula (II) captures water molecules through a hydrolysis reaction. Specifically, moisture around the organic luminescent layer reacts with the Co—O bond of the organo-metallic compound, and the Co converts to a hydroxide form while releasing carboxylic acid, R'COOH. Consequently, 2 moles of water react with 1 mole of the organo-metallic compound of formula (II) to form the hydroxide. The present inventors have found that the organo-metallic compound of formula (II) which functions as described above is indeed an improved water-scavenger that can be used for an organic EL device.

The following Examples and Comparative Example are given for the purpose of illustration only, and are not intended to limit the scope of the invention.

EXAMPLE 1

The compound of formula (VIII) (Compound A) was synthesized as follows:

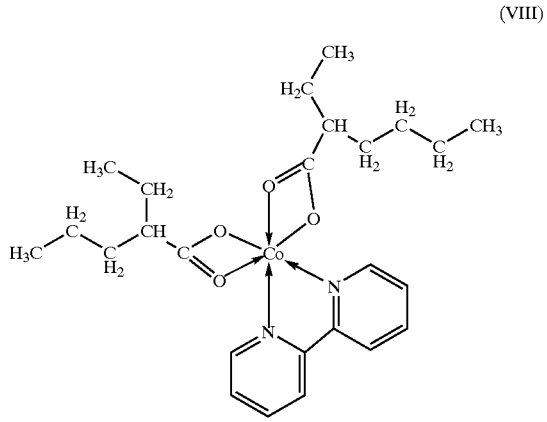

2-ethylhexane was recrystallized from an ethanol-water mixture, and the crystals were filtered and vacuum dried at room temperature. 0.72 g (0.005 mol) of recrystallized 2-ethylhexane and 0.7 g (0.0025 mol) of cobalt sulfate(II) .7hydrate were placed in a 100 ml beaker, 20 ml of unhydrous ethanol was added thereto, and stirred for 30 min. with heating. The reaction solution was filtered through a cellite mat and the filtrate was placed in a 100 ml beaker. Added to another 100 ml beaker were 0.39 g (0.0025 mol) of recrystalized bipyridine and 100 ml of ethanol in order, and stirred for 30 min. with heating. The resulting solution was added to the previously obtained filtrate and refluxed for 4 hrs with stirring. Then, the solution was cooled to room temperature and concentrated with an evaporator, and the precipitated solids were filtered. The solids were washed and vacuum dried at room temperature.

Then, inside a nitrogen glove box, 0.5 g of Compound A obtained was dissolved in 0.5 g of toluene, placed in a 10 ml glass bottle and stoppered.

An organic EL device (1) as shown in FIG. 1 was prepared using Compound A thus obtained. The organic EL device (1) comprises a sealing case which consisted of a rectangular glass plate (2), an enclosing glass cap (3) facing the glass plate and an adhesive sealing part (8). On the whole surface of the glass plate (2) which is a part of the sealing case, a transparent and conductive ITO cathode layer (5) was grown to a thickness of 200 nm by sputtering, and the cathode was patterned into a predetermined shape by photolithography. A part of the cathode (5) extended to the end part of the glass plate (2) to be connected to an operating circuit (not shown in the figure).

The glass plate having the ITO layer was washed, dried, installed in a vacuum deposition apparatus and then evacuated to $10^{-6}$ torr. A 20 nm thick CuPc hole injection layer (4a) was vapor deposited on the anode (5). Then, a 30 nm thick bis(N-(1-naphtyl-n-phenyl))benzidine($\alpha$-NPD) hole transport layer (4b) was laminated on the hole injection layer (4a). Subsequently, a 50 nm thick tris(8-quinolinolato) aluminum(Alq$_3$) luminescent layer/electron transport layer (4c) was laminated on the hole transport layer (4b). An Al—Li alloy upper electrode(cathode) (6) was then formed to a thickness of 200 nm by co-deposition. A part of the cathode (6) extended to the end part of the glass plate (2) to be connected to an operating circuit (not shown in the figure).

A water-scavenging agent layer was disposed in the inner side of the rectangular enclosing cap (3). A 50 wt % solution of the cobalt.amine compound of formula (VIII) in toluene was coated by printing or dropping under a moisture-free dry air atmosphere and dried, to form a transparent organo-metallic compound layer.

A UV-curable epoxy resin (8) constituting the sealing part was coated at the outer periphery of the enclosing cap glass plate, and dried. Under a moisture-free dry air atmosphere, the glass substrate plate carrying the organic luminescent layer and the enclosing cap were arranged to face each other, and the resin was cured through UV irradiation to seal the organic luminescent part having a thickness of 30 $\mu$m.

After sealing, the sealed organic EL device was heated at 100° C. for 1 hr for the purpose of aging for a succeeding reaction with moisture.

An accelerated aging test was performed on the luminescent part of the organic EL device under the condition of 85° C. and 85% humidity to observe the growth of dark spots using a microscope. As shown in FIG. 2, the dark spot diameter was 1 $\mu$m at the beginning and did not become larger even after 100 hrs in contrast to the growing dark spot observed for Comparative Device containing no water-scavenger. Therefore, it is confirmed that the compound of the present invention is an efficient water-scavenger for an organic EL device.

It is noted that the 100 hour test period of the accelerated aging test corresponds to several thousand hours under the usual use condition.

The enclosing cap (3) of the organic EL device (1) in FIG. 1 has the shape of a flat glass plate, but it is not limited thereto, and it may be of a vessel shape of which the outer periphery part for sealing projects into an embossed part and the inner part for holding the water-scavenging means is of an intaglio shape.

EXAMPLE 2

The compound of formula (IX) (Compound B) was synthesized as follows:

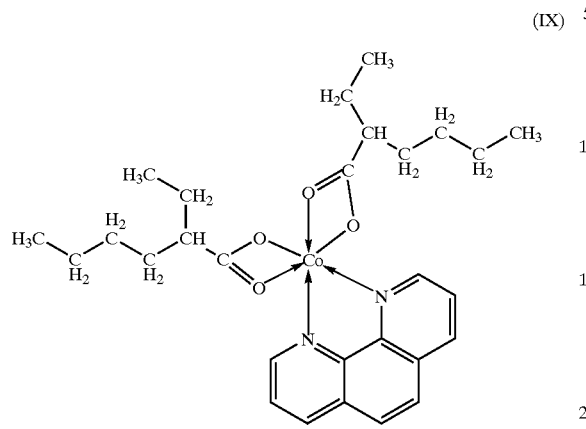

(IX)

2-ethylhexane was recrystallized from an ethanol-water mixture, and the crystals were filtered and vacuum dried at room temperature. 0.72 g (0.005 mol) of recrystallized 2-ethylhexane and 0.7 g (0.0025 mol) of cobalt sulfate(II) .7hydrate were placed in a 100 ml beaker, 20 ml of unhydrous ethanol was added thereto, and stirred for 30 min. with heating. The reaction solution was filtered through a cellite mat and the filtrate was placed in a 100 ml beaker. Added to another 100 ml beaker were 0.45 g (0.0025 mol) of recrystalized 1,10-phenantronine and 100 ml of ethanol in order, and stirred for 30 min. with heating. The resulting solution was added to the previously obtained filtrate and refluxed for 4 hrs with stirring. Then, the solution was cooled to room temperature and concentrated with an evaporator, and the precipitated solids were filtered. The solids were washed with ethanol and vacuum dried at room temperature.

Then, inside a nitrogen glove box, 0.5 g of Compound B obtained was dissolved in 0.5 g of toluene, transferred to a 10 ml glass bottle, and stoppered.

An organic EL device (1) as shown in FIG. 1 was prepared using Compound B obtained thus. The glass plate (2) and the organic luminescent part laminated thereon were the same as those in Example 1.

A glass plate enclosing cap was washed and installed to a vacuum deposition apparatus. The paste obtained by mixing 25% of the cobalt.amine.carboxylic acid composite of formula (IX), 30% of a dye (CuPc), 10% of a synthesized resin and 35% of dry oil using a three-body roller was coated on the inside of the inner enclosing cap using a vapor-deposition mask by a screen printing method according to a preset pattern and dried, to obtain a transparent organo-metallic compound water-scavenger layer.

The enclosing cap (3) was heated at 150° C. for 20 min under dry nitrogen to remove the solvent. After drying, a UV-curable epoxy adhesive was coated at the outer periphery of the enclosing cap. The glass plate on which the organic luminescent layer was formed and the enclosing cap were arranged to face each other, and the resin was cured by UV irradiation. The organic EL device thus obtained was heated at 100° C. in an oven to let the water-scavenger absorb residual moisture remaining in the device.

An accelerated aging test of the luminescent part of the organic EL device was conducted under the condition of 85° C. and 85% humidity to observe the growth of dark spots using a microscope. As shown in FIG. 2, the dark spot diameter was 1 μm at the beginning and did not become significantly larger even after 100 hrs, which should be compared with Comparative Example having no water-capturing agent. Therefore, it is confirmed that the compound of the present invention performs a satisfactory water-scavenging function for an organic EL device.

EXAMPLE 3

The cobalt.amine.carboxylic acid composite of formula (X) (Compound C), $Co(COOC_7H_{15})_2(BDEA)_2$ (BDEA= butyldiethanolamine), was employed as a water-scavenger. The glass plate (2) and the organic luminescent part laminated thereon were the same as those in Example 1.

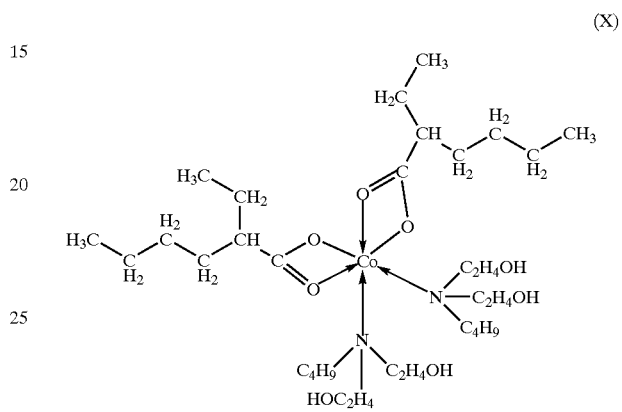

(X)

The compound of formula (X) (Compound C) was synthesized as follows:

2-ethylhexane was recrystallized from an ethanol-water mixture, and the crystals were filtered and vacuum dried at room temperature. 0.72 g (0.005 mol) of recrystallized 2-ethylhexane and 0.7 g (0.0025 mol) of cobalt sulfate(II) .7hydrate were placed in a 100 ml beaker, 20 ml of unhydrous ethanol was added thereto, and stirred for 30 min. with heating. The reaction solution was filtered through a cellite mat and the filtrate was placed in a 100 ml beaker. Added to another 100 ml beaker were 0.81 g (0.005 mol) of recrystalized butyldiethanolamine and 100 ml of ethanol in order, and stirred for 30 min. with heating. The resulting solution was added to the previously obtained filtrate and refluxed for 4 hrs with stirring. Then, the solution was cooled to room temperature and concentrated with an evaporator, and the precipitated solids were filtered. The solids were washed with ethanol and vacuum dried at room temperature.

Then, inside a nitrogen glove box, 0.5 g of Compound C obtained was dissolved in 0.5 g of toluene, transferred to a 10 ml glass bottle, and stoppered.

An accelerated aging test of the luminescent part of the organic EL device was conducted under the condition of 85° C. and 85% humidity to observe the growth of dark spots using a microscope. As shown in FIG. 2, the dark spot diameter was 1 μm at the beginning and did not become significantly larger even after 100 hrs, which should be compared with Comparative Example having no water-capturing agent. Therefore, it is confirmed that the compound of the present invention performs a satisfactory water-scavenging function for an organic EL device.

EXAMPLE 4

The manganese.amine.carboxylic acid composite of formula (XI) (Compound D), $Mn(COOC_7H_{15})_2(BPY)$ (BPY= 2,2'-bipyridyl), was employed as a water-scavenging agent.

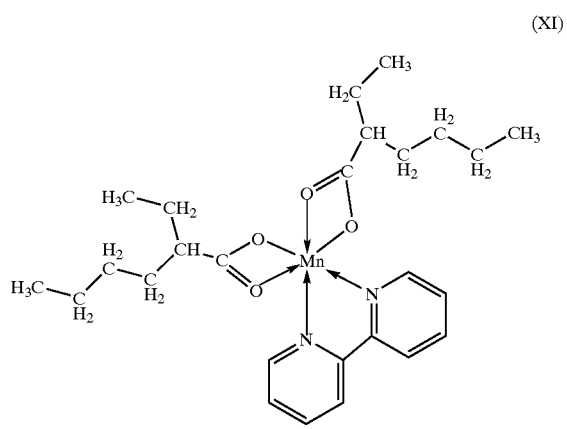

(XI)

The compound of formula (XI) (Compound D) was synthesized as follows:

2-ethylhexane was recrystallized from an ethanol-water mixture, and the crystals were filtered and vacuum dried at room temperature. 0.72 g (0.005 mol) of recrystallized 2-ethylhexane and 0.6 g (0.0025 mol) of cobalt sulfate(II) .5hydrate were placed in a 100 ml beaker, 20 ml of unhydrated ethanol was added thereto, and stirred for 30 min. with heating. The reaction solution was filtered through a cellite mat and the filtrate was placed in a 100 ml beaker. Added to another 100 ml beaker were 0.39 g (0.0025 mol) of recrystalized bipyridine and 100 ml of ethanol in order, and stirred for 30 min. with heating. The resulting solution was added to the previously obtained filtrate and refluxed for 4 hrs with stirring. Then, the solution was cooled to room temperature and concentrated with an evaporator, and the precipitated solids were filtered. The solids were washed with ethanol and vacuum dried at room temperature.

Then, inside a nitrogen glove box, 0.5 g of Compound D obtained was dissolved in 0.5 g of toluene, transferred to a 10 ml glass bottle, and stoppered.

The glass plate having the ITO layer was washed, dried, installed in a vacuum deposition apparatus and then evacuated to $10^{-6}$ torr. A 20 nm thick CuPc hole injection layer (4a) was vapor deposited on the anode (5). Then, a 30 nm thick bis(N-(1-naphtyl-n-phenyl))benzidine(α-NPD) hole transport layer (4b) was laminated on the hole injection layer (4a). Subsequently, a 50 nm thick tris(8-quinolinolato) aluminum($Alq_3$) luminescent layer/electron transport layer (4c) was laminated on the hole transport layer (4b). An Al—Li alloy upper electrode(cathode) (6) was then formed to a thickness of 200 nm by co-deposition. A part of the cathode (6) extended to the end part of the glass plate (2) to be connected to an operating circuit (not shown in the figure).

A water-scavenging agent layer was disposed in the inner side of the rectangular enclosing cap (3). A 50 wt % solution of the cobalt.amine compound of formula (IX) in toluene was coated by printing or dropping under a moisture-free dry air atmosphere and dried, to form a transparent organometallic compound layer.

A UV-curable epoxy resin (8) constituting the sealing part was coated at the outer periphery of the enclosing cap glass plate, and dried. Under a moisture-free dry air atmosphere, the glass substrate plate carrying the organic luminescent layer and the enclosing cap were arranged to face each other, and the resin was cured through UV irradiation to seal the organic luminescent part having a thickness of 30 μm.

After sealing, the sealed organic EL device was heated at 100° C. for 1 hr for the purpose of aging for a succeeding reaction with moisture.

An accelerated aging test of the luminescent part of the organic EL device was conducted under the condition of 85° C. and 85% humidity to observe the growth of dark spots using a microscope. As shown in FIG. 2, the dark spot diameter was 1 μm at the beginning and did not become larger even after 100 hrs in contrast to the growing dark spot observed for Comparative Device containing no water-scavenger. Therefore, it is confirmed that the compound of the present invention is an efficient water-scavenger for an organic EL device.

EXAMPLE 5

The manganese.amine.carboxylic acid composite of formula (XII) (Compound E), $Mn(COOC_7H_{15})_2(PHEN)$ (PHEN=1,10-phenantronine), was employed as a water-scavenger. The glass plate (2) and the organic luminescent part laminated thereon were the same as those in Example 1.

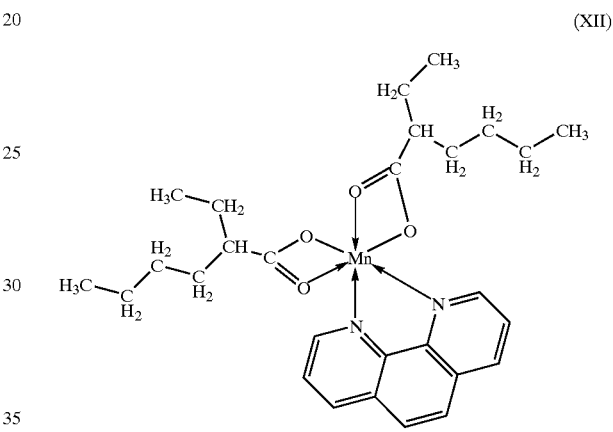

(XII)

The compound of formula (XII) (Compound E) was synthesized as follows:

2-ethylhexane was recrystallized from an ethanol-water mixture, and the crystals were filtered and vacuum dried at room temperature. 0.72 g (0.005 mol) of recrystallized 2-ethylhexane and 0.6 g (0.0025 mol) of cobalt sulfate(II) .5hydrate were placed in a 100 ml beaker, 20 ml of unhydrated ethanol was added thereto, and stirred for 30 min. with heating. The reaction solution was filtered through a cellite mat and the filtrate was placed in a 100 ml beaker. Added to another 100 ml beaker were 0.45 g (0.0025 mol) of recrystalized 1,10-phenantronine and 100 ml of ethanol in order, and stirred for 30 min. with heating. The resulting solution was added to the previously obtained filtrate and refluxed for 4 hrs with stirring. Then, the solution was cooled to room temperature and concentrated with an evaporator, and the precipitated solids were filtered. The solids were washed with ethanol and vacuum dried at room temperature.

Then, inside a nitrogen glove box, 0.5 g of Compound E obtained was dissolved in 0.5 g of toluene, transferred to a 10 ml glass bottle, and stoppered.

EXAMPLE 6

The manganese-amine-carboxylic acid composite of formula (XIII) (Compound F), $Mn(COOC_7H_{15})_2(BDEA)$ (BDEA=butyldiethanolamine), was employed as a water-scavenger. The glass plate (2) and the organic luminescent part laminated thereon were the same as those in Example 1.

(XIII)

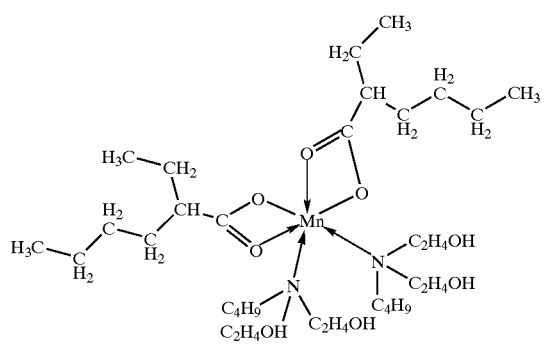

The compound of formula (XIII) (Compound F) was synthesized as follows:

2-ethylhexane was recrystallized from an ethanol-water mixture, and the crystals were filtered and vacuum dried at room temperature. 0.72 g (0.005 mol) of recrystallized 2-ethylhexane and 0.6 g (0.0025 mol) of cobalt sulfate(II) .5hydrate were placed in a 100 ml beaker, 20 ml of unhydrous ethanol was added thereto, and stirred for 30 min. with heating. The reaction solution was filtered through a cellite mat and the filtrate was put into 100 ml of a beaker. Added to another 100 ml beaker were 0.81 g (0.005 mol) of recrystalized butyldiethanolamine and 100 ml of ethanol in order, and stirred for 30 min. with heating. The resulting solution was added to the previously obtained filtrate and refluxed for 4 hrs with stirring. Then, the solution was cooled to room temperature and concentrated with an evaporator, and the precipitated solids were filtered. The solids were washed with ethanol and vacuum dried at room temperature.

Then, inside a nitrogen glove box, 0.5 g of Compound F obtained was dissolved in 0.5 g of toluene, transferred to a 10 ml glass bottle, and stoppered.

COMPARATIVE EXAMPLE

The procedure of Example 1 was repeated except that a water-scavenger was not used, to prepare an organic EL device having the same structure as in Example 1.

An accelerated aging test of the luminescent part of the organic EL device was conducted under the condition of 85° C. and 85% humidity to observe the growth of dark spots using a microscope. As shown in FIG. 2, the dark spot diameter was 1 µm at the beginning, but it very quickly grew to become 50 µm or larger and was recognized with the naked eye after 100 hrs.

As described above, in accordance with the present invention, the following effects may be gained by way of using an organic compound of formula (I) as a water-scavenger for an organic EL device;

1) the growth of dark spots is prevented, which remarkably improves the operating life of the organic EL device.

2) the inventive water-scavenging agent can be dissolved in a polar solvent and coated by a printing method, resulting in enhanced work efficiency.

3) it is possible to form both the inventive enclosing cap and substrate glass plate using a same material, which makes it easy to select an adhesive for the sealing part.

4) the coating of the water-scavenging agent by printing eliminates the need to form an intaglio to hold a water-scavenging agent in the enclosing cap, and therefore, the use of a mold or a mask is not necessary.

5) the water-scavenging agent layer may be formed in close proximity to the luminescent part, which enhances the water-scavenging effect and makes the space within the package smaller, thereby reducing the amount of residual moisture remaining in the package.

6) in case of an organic EL device of the top emission type which emits light through the enclosing cap, the water-scavenging layer can function as a color filter to provide a simple, color organic EL device.

While the invention has been described with respect to the above specific embodiments, it should be recognized that various modifications and changes may be made to the invention by those skilled in the art which also fall within the scope of the invention as defined by the appended claims.

What is claimed is:

1. A water-scavenging agent for an organic EL device comprising a compound selected from the group consisting of:

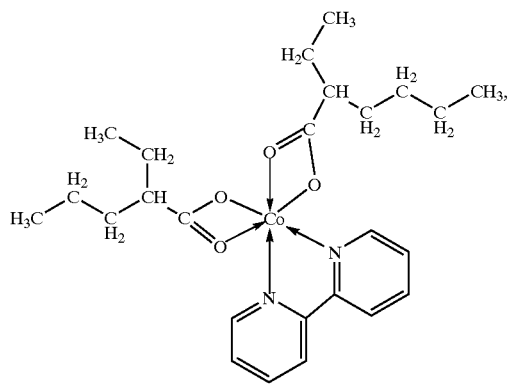

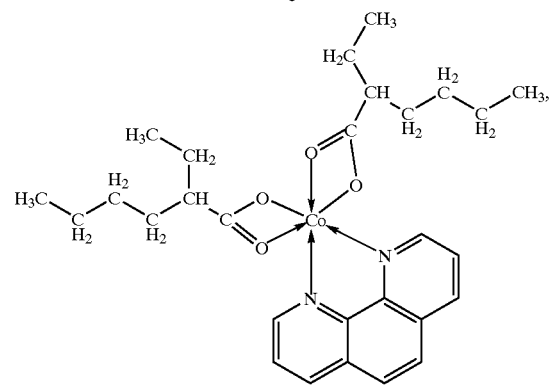

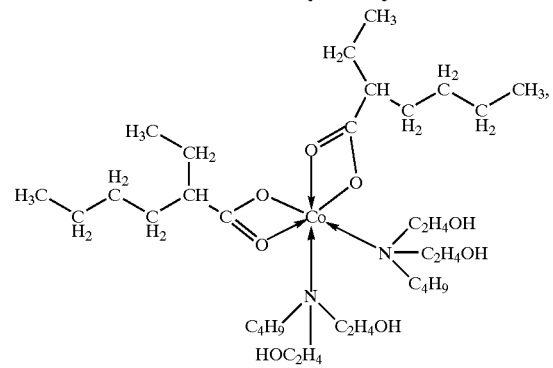

-continued

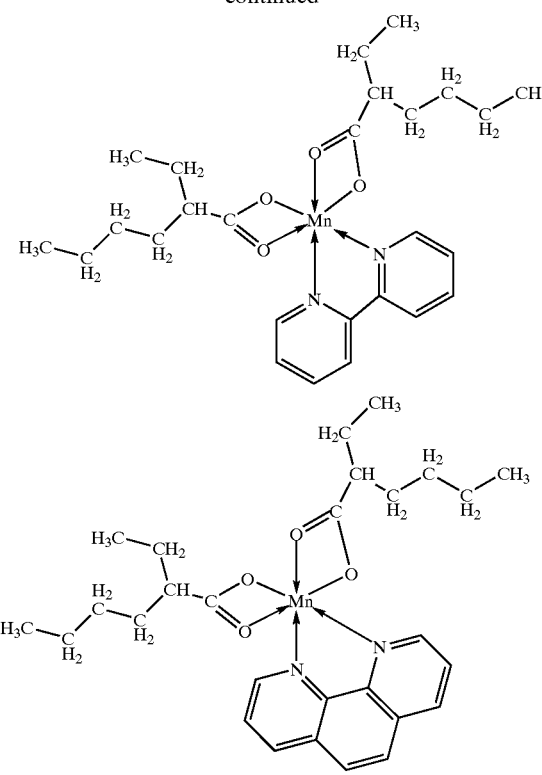

and

-continued

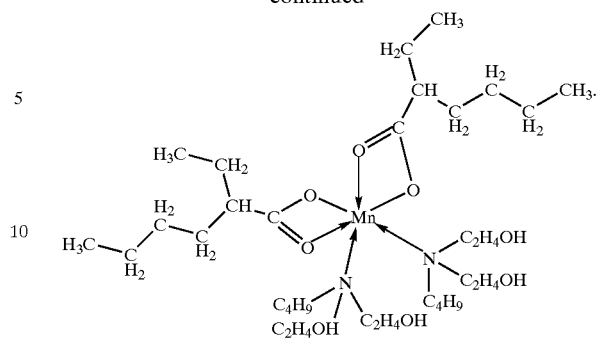

2. An organic EL device which comprises a glass substrate plate having an organic luminescent part, a sealing case having a cap to be sealed with said glass plate to enclose said organic luminescent part and a water-scavenging means installed inside said sealing case, the water-scavenging means containing the water-scavenging agent of claim 1.

3. The organic EL device of claim 2, wherein the water-scavenging agent is in the form of a layer coated on the inner wall of the sealing case.

4. The organic EL device of claim 2, wherein the water-scavenging agent is in the form of a powder held inside the sealing case.

\* \* \* \* \*